United States Patent [19]

Ito et al.

[11] 3,932,615

[45] Jan. 13, 1976

[54] PROCESS FOR THE PREPARATION OF GRANULES

[75] Inventors: Shojiro Ito, Ebina; Akira Takami, Atsugi; Tokio Takekoshi, Machida, all of Japan

[73] Assignee: Meiji Seika Co., Ltd., Japan

[22] Filed: Mar. 8, 1974

[21] Appl. No.: 449,445

[30] Foreign Application Priority Data

Mar. 16, 1974 Japan.............................. 48-30073

[52] U.S. Cl. ...................... 424/80; 127/29; 127/63; 424/181; 424/227; 424/271; 424/176; 424/361
[51] Int. Cl.² ......................................... A61K 31/00
[58] Field of Search ............ 127/29, 30, 63; 424/35, 424/176, 271, 361, 181, 80

[56] References Cited
UNITED STATES PATENTS

| | | | |
|---|---|---|---|
| 2,936,307 | 5/1960 | Johnson | 424/181 X |
| 3,079,303 | 2/1963 | Raff | 424/35 X |
| 3,212,908 | 10/1965 | Childs | 127/63 X |
| 3,305,447 | 2/1967 | Reimers | 127/63 X |
| 3,351,527 | 11/1967 | Apat | 424/80 X |
| 3,485,914 | 12/1969 | Corn | 424/80 X |
| 3,557,280 | 1/1971 | Weber | 424/80 |
| 3,619,292 | 11/1971 | Brouillard | 127/29 |
| 3,639,169 | 2/1972 | Broeg | 127/29 |
| 3,781,268 | 12/1973 | Kawaguchi | 424/181 X |
| 3,783,159 | 1/1974 | Guadagnini | 424/181 |
| 3,802,915 | 4/1974 | Gupta | 127/63 |
| 3,825,528 | 7/1974 | Vogan | 424/181 X |
| 3,855,411 | 12/1974 | Bahal | 424/176 |

*Primary Examiner*—Morris O. Wolk
*Assistant Examiner*—Sidney Marantz
*Attorney, Agent, or Firm*—McGlew and Tuttle

[57] ABSTRACT

Granules are prepared by subjecting a crystalline sugar, a basis, adjuvants and a binder-containing solution to a mixing apparatus, followed by crushing and drying by conventional techniques. The resultant products are characterized by having a uniform granular size, good disintegrating properties, relatively great apparent density and abrasion resistance. The basis comprises at least one member selected from the group of penicillin, tetracycline, movobiocin, kanamycin, paromomycin and midecamycin.

9 Claims, No Drawings

PROCESS FOR THE PREPARATION OF GRANULES

BACKGROUND OF THE INVENTION

1. Field of the Invention

This invention relates to a method for preparing granules having a uniform granule size, good disintegrating properties, relatively great apparent density and abrasion resistance by subjecting a crystalline sugar, a basis, adjuvants and a binder-containing solution to a mixing apparatus, whereby the crystalline sugar is coated with the basis and adjuvants to form granules of a uniform particle size.

2. Prior Art

In general, granule or particle products have been heretofore prepared by powdering raw materials such as a basis and some suitable adjuvants, mixing the powdered material with a corrigent such as powdered sugar under wetting conditions, and granulating the mixture by means of an extruder-type or crushing type granulator.

The just-mentioned prior-art method is, however, defective in that: (1) The yield of the granule product becomes low due to substantial loss of the powdered material in the binding stage and, if a binder is used in a larger amount so as to raise the yield, the ultimate granular product will be deteriorated in disintegratability and solubility; (2) It is difficult to produce granules of uniform size and relatively great apparent density, and the commercial value of the products is lowered due to undesirably wide distribution of granule sizes and inconveniences in handling; and (3) A great number of production steps and manual operations are required, causing frequent operational troubles.

In order to overcome these defects, many improved methods have been proposed by introducing new apparatus of different types, including the method using a fluidized bed granulation apparatus and the method of coating core material with a sprayed suspension with use of a coating apparatus. However, the last-metioned coating method has a vital disadvantage that it requires a solvent in such a large amount that may spoil the working conditions with increased possibility of risky accidents, such as fire, explosion and the like, and also may give rise to environmental pollution. In addition, an enormous cost is required for installation of the facilities for collecting the solvent in order to prevent environmental pollution. Moreover, the spraying method has also the disadvantage that it is difficult to coat the core material completely with a powdery material. This results in reduction in yield and undesirably requires provision of a fine powder-collecting apparatus. Furthermore, the coated material is easily excoriated from the ultimate product even by slight friction, such as, for example, that occurred by sieving, due to insufficient binding between the core material and the coat, thus spoiling the commercial value of the product.

DETAILED DESCRIPTION OF THE INVENTION

The present inventors conducted a research on the method for the preparation of granular medicinal agents, which can overcome the prior-art's disadvantages and by which granules having a uniform particle size can be produced. As a result, the present inventors have accomplished a novel method which can solve the problems inherent to the prior-art methods as mentioned above. The method of the present invention can be put into practice by means of a conventional mixing apparatus with use of a binder-containing solution in an amount 10 times smaller than that needed by the spraying method. The yield of the ultimate product is almost 100% since the starting powdery materials are hardly lost during the production process. Furthermore, strong binding of the crystalline sugar to the basis and the adjuvants can be attained, without allowing easy separation of the basis and adjuvants from the sugar cores by slight friction.

The method of the present invention comprises mixing crystalline sugar, a basis and adjuvants in the presence of a binder-containing solution in a suitable mixing apparatus.

The method of the present invention is particularly suitable for the preparation of a granule using sugar, particularly crystalline sugar, as the core material and a basis with or without other adjuvants as the coating material. In general, sucrose is used as the crystalline sugar, but any other sugar that is water-soluble and forms crystals of excellent physical and mechanical strengths, such as glucose, fructose, lactose or the like may also be employed.

The granule or particle size of the crystalline sugar may be varied within a wide range depending upon the particular requirements of the ultimate product, but is preferably within the range of $177\mu$ (passing a sieve of No. 80 prescribed in the Eighth Pharmacopoeia of Japan) to $500\mu$ (passing a No. 32 sieve) in consideration of the appearance of the ultimate product and the prevention of the adhesion of fine crystalline sugar particles to wall surface of the vessel due to static electricity. The crystalline sugar is added in an amount greater than 70%, preferably about 75 – 90%, so as to produce an ultimate product of good appearance at a high yield.

The basis which coats the crystalline sugar may be of any type which allows combination with the sugar without difficulty, for example, a penicillin such as penicillin V, ampicillin, phenethicillin, propicillin, cloxacillin or cycloxacillin, another antibiotic such as tetracycline, novobiocin, kanamycin, paromomycin, medecamycin, kitasamycin, spiramycin, triacetylorleandomycin or the like, a cold remedy, an antipyretics, an analygesics, an antitussive, an expectorant, a vitamin complex or the like. The coating powder materials are generally used in an amount less than 30%, preferably about 25 – 10%.

Furthermore, adjuvants such as stabilizers, corrigents, flavoring agents or the like which are generally employed in the preparation of pharmaceutical compositions may be coated to the core material along with the basis.

The process for coating the core material with the basis either alone or in combination with adjuvants is carried out in a suitable mixing apparatus while adding thereto a binder solution. The solvent should not be of the nature that can dissolve or decompose the basis, crystalline sugar and other adjuvants and preferably boils at as low as 35° – 70°C. Examples of the solvent include chloroform, dichloromethane, methanol and the like. The binder should be soluble in the organic solvent and should not affect the stability of the other constituents of the granule to be prepared. Examples of the binder are hydroxypropylcellulose (HPC), polyvinylpyrrolidone (PVP), methylcellulose and the like, and the amount of the binder is preferably within the range of 0.1 – 3.0%.

An important feature of the present invention is that the coating is carried out in a mixing apparatus but not by a known coating system. The mixing means is not restricted to a special type so long as it has no crushing function; examples of the feasible mixers including a sigma-blade type mixer such as dough mixer, kneader or mass mixer, etc., vertical-shaft type mixer such as Glen powder mixer, Banno mixer or Hobart mixer, etc., ribbon-blade type mixer such as ribbon mixer, etc., Henschell mixer and the like. Particularly, the dough mixer is superior in mixing and coating efficiency.

It is due to the use of a mixer that makes it possible to provide satisfactory coatings of the basis on the surface of the crystalline sugar.

In the mixer, the crystalline sugar which has been uniformly granulated to a size substantially corresponding to the size of the ultimate granule or particle product is sufficiently mixed with a powdered basis and a stabilizer or some other required adjuvants. Then, a binder solution is added to the resultant mixture for mixing under wetting or moistening conditions. The resultant semi-dried mixture in the form of lump is reduced into granules or particles of the desired size by means of a crushing granulator (rotating knife-blade type) under such a gentle condition that will not pulverize the sugar crystals per se into pieces, followed by drying to obtain a granule or particle product.

There are no particular requirements on the combination order of the starting materials, but it is preferable that a half of the crystalline sugar is first charged into the mixer, followed by the basis, adjuvants and another half of the crystalline sugar, so as to raise the mixing efficiency by preventing adhesion of the basis to the corners of a non-circular mixer such as dough mixer or to the joints of the agitator blades.

As has been clear from the above, the use of crystalline sugar as a core material leads to easy production of a granular material or product having a uniform granule size in a mixer. The granular product of the present invention has the following advantages:

i. Ready availability of a granular product of uniform and desired size owing to the use of a core material having a preset granule size corresponding to the product;

ii. Excellent disintegratability and solubility when used as a dry syrup;

iii. Relatively great apparent density, that is, small in volume per dose, this enable one to handle it advantageously;

iv. The coating basis coats firmly onto the crystalline sugar and can not be easily excoriated therefrom, as with the granules which are prepared by a conventional method, owing to slight friction caused, for example, when passed through a sieve.

The present invention will be particularly illustrated in the following examples, which are shown by way of illustration only.

EXAMPLE 1

44.3 Kg of crystalline sucrose having a particle size range of 150 – 400 $\mu$ was introduced into a dough mixer, Jushin Tekkosho Model WN-170SU, to which were further added with sufficient agitation 5.0 Kg of penicillin V and a finely powdered mixture consisting of 200 g of saccharin sodium, 200 g of sodium chloride and 150 g of peach flavor. While mixing for 20 minutes, 7.0 liters of the dichloromethane solution which contains 0.15 Kg of hydroxypropylcellulose was added dropwise to the resultant mixture for wetting. The wetted mixture were crushed by means of a speed mill, Showa Engineering KK, Model D-50, and dried under vacuum to obtain a granular product. The yield was 98.5% when calculated according to the following equation:

$$\text{Yield (\%)} = \frac{\text{Weight of the product similar in particle size to the original crystalline sugar}}{\text{Total weight of the materials subjected to the mixer except the binder solvent}} \times 100$$

EXAMPLE 2

Example 1 was repeated using a universal mixer, Haagen & Rinau Model RU-200. The yield was 97%.

EXAMPLE 3

Example 1 was repeated on 1/50 scale using a ribbon mixer, Fuji Denki Kogyo Model 5DM-r. The yield was 96.0%.

EXAMPLE 4

Example 1 was repeated on 1/50 scale using a Banno mixer, Shinagawa Kogyosho Model 5DM-r. The yield was 96.0%.

EXAMPLE 5

700 g of crystalline sucrose having a particle range of 400 – 850$\mu$ was introduced into a kneader, Fuji Powder Model KDHJ-10, to which were further added under sufficient mixing 67 g of tetracycline, 33 g of novobiocin calcium and a finely powdered mixture composed of 100 g of sodium metaphosphate, 3 g of saccharin sodium, 8 g of banana flavor and 69 g of corn starch. And then, while mixing for 10 minutes, 150 ml of the chloroform solution containing 20 g of polyvinylpyrrolidone was added dropwise to the mixture for wetting. The resultant mixture was crushed by means of a speed mill, followed by vacuum drying to obtain a granular product. The yield was 96.0%.

EXAMPLE 6

Example 5 was repeated except that 100 g of crystalline sucrose was replaced by the same amount of corn starch. The yield was 86%.

EXAMPLE 7

Example 5 was repeated except that 200 g of crystalline sucrose was replaced by the same amount of corn starch. The yield was 70.0%.

EXAMPLE 8

880 g of crystalline sucrose having a particle size range of 300 – 700$\mu$ was place in a kneader, Fuji Powder Model KDHJ-10, to which were added 25 g of penicillin V and a finely powdered mixture consisting of 4 g of saccharin sodium, 4 g of sodium chloride, 3 g of peach flavor and 82 g of corn starch under sufficient mixing condition. And then, while mixing for 10 minutes, 150 ml of 1:1 mixture of absolute methanol and dichloromethane containing 2 g of methylcellulose was added dropwise to the mixture for wetting. The resultant wetted mixture was crushed by means of a speed mill and vacuum-dried to yield a granule product. The yield was 99.0%.

EXAMPLE 9

Example 8 was repeated using a Banno mixer, Shinagawa Kogyosho Model 5DM-r. The yield was 97.5%.

EXAMPLE 10

Example 8 was repeated using a Henschell mixer, Henschell Model FM 10/L. The yield was 95.0%.

We claim:

1. Process for the preparation of granular product of uniform particle size, good disintegrating properties, relatively great apparent density and abrasion resistance, which comprises the steps of: (a) mixing a crystalline sugar and a finely powdered basis having a particle size of from about $177\mu$ to about $500\mu$ in a mixing apparatus in the presence of about 15% by weight based on the total combined weight of said sugar and said basis of a solution containing from about 0.1 to 3.0% by weight of binder based on the same total combined weight, said basis comprising at least one member selected from the group consisting of penicillin, tetracycline, novobiocin, kanamycin, paromomycin and midecamycin; (b) crushing the resultant wetted mixture of sugar, basis and binder solution in the form of lumps; and (c) removing the remaining solvent from the said solution of the binder, and recovering the granular product therefrom.

2. Process according to claim 1, wherein the ratio by weight of said crystalline sugar to said basis and, if any, adjuvants is 70 – 90 : 30 – 10, and preferably, 75 – 90 : 25 – 10.

3. Process according to claim 1, wherein said crystalline sugar comprises at least one member selected from the group consisting of sucrose, fructose, glucose and lactose.

4. Process according to claim 1, wherein said binder comprises at least one member selected from the group consising of hydroxypropylcellulose, polyvinylpyrrolidone and methylcellulose.

5. Process according to claim 1, wherein said basis also includes at least one member selected from the group consisting of stabilizers, corrigents and flavoring agents.

6. Process according to claim 1, wherein said mixing is carried out in a sigma-blade type mixer, a ribbon-blade type mixer, a vertical-shaft type mixer, or a Henschell mixer.

7. Process according to claim 6, wherein said mixing is carried out with a sigma-blade type mixer which is a dough mixer, a kneader, or a mass mixer.

8. Process according to claim 6, wherein said mixing is carried out with a vertical-shaft type mixer which is a Glen powder mixer, a Hobart mixer, or a Banno mixer.

9. Process according to claim 6, wherein said mixing is carried out with a ribbon-blade type mixer which is a ribbon mixer.

* * * * *